US009435735B1

(12) United States Patent
Dziura (10) Patent No.: US 9,435,735 B1
(45) Date of Patent: Sep. 6, 2016

(54) OPTICAL PARAMETRIC MODEL OPTIMIZATION

(71) Applicant: Thaddeus Gerard Dziura, San Jose, CA (US)

(72) Inventor: Thaddeus Gerard Dziura, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 660 days.

(21) Appl. No.: 13/889,655

(22) Filed: May 8, 2013

Related U.S. Application Data (60) Provisional application No. 61/644,147, filed on May 8, 2012.

(51) Int. Cl.
*G06F 19/00* (2011.01)
*G01N 21/47* (2006.01)

(52) U.S. Cl.
CPC .......... *G01N 21/4788* (2013.01); *G01N 21/47* (2013.01)

(58) Field of Classification Search
CPC ............ G01N 21/4788; G01N 21/253; B01L 3/5085
USPC .......................................... 702/181–185, 188
See application file for complete search history.

(56) References Cited

U.S. PATENT DOCUMENTS

| 8,090,558 | B1 | 1/2012 | Dziura | |
| 2008/0059141 | A1* | 3/2008 | Finarov et al. | ................. 703/13 |

OTHER PUBLICATIONS

Benjamini, Yoav et al. "Controlling the False Discovery Rate: A Practical and Powerful Approach to Multiple Testing", Journal of the Royal Statistical Society, Series B (Methodological), vol. 57, No. 1 (1995), pp. 289-300.
Foster, Dean, et al. "Alpha-Investing Sequential Control of Expected False Discoveries", Department of Statistics, Wharton School of the University of Pennsylvania, Joint Statistics Meeting, Salt Lake City, Aug. 2007.
Foster, Dean P., et al., "Alpha-investing: A procedure for sequential control of expected false discoveries", Department of Statistics, The Wharton School of the University of Pennsylvania, Jul. 24, 2007, 26 pages.
Soric, Branko, "Statistical Discoveries and Effect-Size Estimation", Journal of the American Statistical Association, Jun. 1989, vol. 84, No. 406, Theory and Methods.

* cited by examiner

*Primary Examiner* — Edward Raymond
(74) *Attorney, Agent, or Firm* — Blakely Sokoloff Taylor & Zafman, LLP (57) ABSTRACT

Provided are scatterometry model optimizations for evaluating a diffracting structure. In one embodiment, a method includes identifying one or more parameters to test for inclusion in the model. The method includes computing a difference between modeled data generated with the one or more parameters and measured data. The one or more parameters are included in the model in response to a reduction in the difference between the modeled data and the measured data compared to previous modeled, and passing a statistical hypothesis test. In one embodiment, the one or more parameters pass the statistical hypothesis test in response to the probability of obtaining the reduction in the difference is less than a significance level. In one embodiment, the significance level is a function of an alpha wealth value. In one embodiment, the method includes ordering the plurality of parameters for testing according to one or more criteria.

21 Claims, 7 Drawing Sheets

OPTICAL PARAMETRIC MODEL OPTIMIZATION

PRIORITY

This application is a Non-Provisional of, claims priority to, and incorporates by reference in its entirety for all purposes, the U.S. Provisional Patent Application No. 61/644,147 filed May 8, 2012.

TECHNICAL FIELD

Embodiments of the invention pertain to scatterometry and more particularly to evaluation of a diffracting structure.

BACKGROUND

Optical metrology techniques generally referred to as scatterometry offer the potential to characterize a workpiece (i.e., a sample) during a manufacturing process. In practice, light is directed onto a periodic grating formed in a workpiece and spectra of reflected light are measured and analyzed to characterize the grating. Characterization parameters may include critical dimensions (CDs), sidewall angles (SWAs) and heights (HTs) of gratings, material dispersion parameters, layer thicknesses, angle of incidence of light directed onto the diffracting structure, calibration parameters of an optical measurement system, etc., which affect the polarization and intensity of the light reflected from or transmitted through a material.

Figure 1:
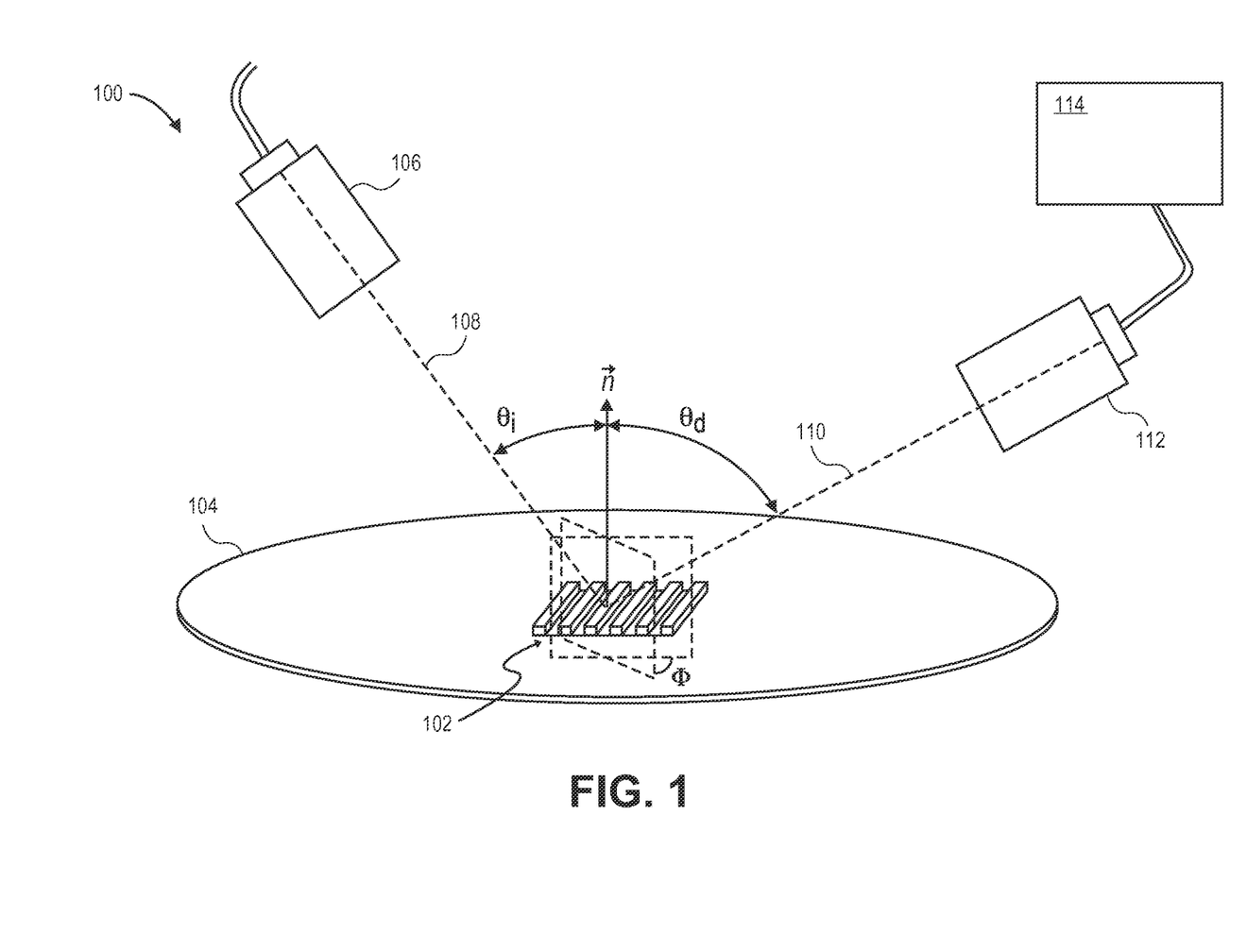
FIG. 1 depicts an exemplary optical metrology system for scatterometry.

Characterization of the grating may thereby characterize the workpiece as well as manufacturing process employed in the formation of the grating and the workpiece. For example, the optical metrology system 100 depicted in FIG. 1 can be used to determine the profile of a grating 102 formed on a semiconductor wafer 104. The grating 102 can be formed in test areas on the wafer 104, such as adjacent to a device formed on the wafer 104. The optical metrology system 100 can include a photometric device with a source 106 and a detector 112. The grating 102 is illuminated by an incident beam 108 from source 106. In the present exemplary embodiment, the incident beam 108 is directed onto the grating 102 at an angle of incidence $\theta_i$ with respect to normal of the grating 102 and an azimuth angle $\phi$ (e.g., the angle between the plane of incidence of beam 108 and the direction of the periodicity of the grating 102). A diffracted beam 110 leaves at an angle of $\theta_d$ with respect to normal and is received by the detector 112. The detector 112 converts the diffracted beam 110 into a measured metrology signal. To determine the profile of the grating 102, the optical metrology system 100 includes a processing module 114 configured to receive the measured metrology signal and analyze the measured metrology signal.

Analysis of measured spectra generally involves comparing the measured sample spectra to simulated spectra to deduce a scatterometry model's parameter values that best describe the measured sample. As used herein, "model" refers to a scatterometry model and "parameter" refers to a model parameter of the scatterometry model unless otherwise specified. A model can include a film model, optical CD model, composition model, overlay model, or any other optical model or combination thereof.

Existing methods of determining which parameters to include or exclude in a model require a user (e.g., an engineer performing the regression analysis) to determine model fit metrics at one or more data points, subjectively analyze the model fit metrics, and revise the model based on the user's subjective assessment. For example, the user would document chi-square of the one or more data points, make a subjective determination regarding whether chi-square was sufficiently low, then revise the model if chi-square was not sufficiently low. This process of discovery typically involves determining: 1) the materials in the structure that the optical constants should be adjusted for; (2) for which materials in the layer the optical constants are varying; (3) which dimensional parameters are changing across the wafer; (4) and for which model parameters the metrology tool provides sufficient sensitivity and minimal parameter correlation, therefore justifying floating them in the model. The user could also review trends in model parameters across the wafer, and compare them against expected within-wafer variations based on known process signatures from, for example, etch or deposition tools. Such subjective determinations are typically based on previous experience with other projects and models, and qualitative assessments of whether the model fit to the data appears to be subjectively good enough. Thus, the existing process of optimizing the model cannot easily be automated, leading to greater cost, time, and inconsistencies in model generation and evaluation of the diffracting structure.

One technique of model optimization is disclosed by U.S. Pat. No. 8,090,558, "Method for optical parametric model optimization," which is incorporated by reference for all purposes. U.S. Pat. No. 8,090,558 describes a method for determining which parameters are to be floated, set, or discarded from the model, which includes determining whether average chi-square and chi-square uniformity decrease or increase when a parameter is added to the model. While this method provides for a more systematic approach and demonstrates more efficient model optimization than previous techniques, techniques such as this do not focus on guidelines regarding how large an average chi-square improvement, or how low a value of chi-square uniformity, is necessary to justify a model change. The decision of which parameters to include or remove and when to terminate the optimization is left to the subjective judgment of the data analyst. In addition to being based on subjective judgment, such existing techniques do not guard against noise parameters (i.e., insignificant parameters) from being added to the model.

Some existing methods allow a user to test the addition of a single parameter to the model, but are inadequate for testing repeated model changes with the same set of data. This is the so-called "multiple comparisons problem." Statistical significance tests, such as the F-test, were not designed for repeated model changes, and can result in false assessments of the significance level. Various modifications have been proposed for dealing with the multiple comparisons problem (e.g., the "Bonferroni correction" & "Family Wise Error Rate"), but are less than ideal. The Bonferroni correction is generally regarded as being too conservative, and may reject some parameters that should be included in the model. Family Wise Error Rate methods were developed for conducting just a few tests, and not a large number of tests.

Other existing methods seek to control the probability over a number of significance tests that a noise parameter has been added rather than seeking to ensure that no noise parameters are added to a model. Such methods can be more appropriate in fields with large scale testing for which the number of potential model parameters that could be tested is large, but less appropriate for applications with fewer model parameters in which it may be desirable to prevent noise parameters from being added to the model.

Thus, existing methods are subjective and therefore require large amounts of user input, and fail to guard against insignificant parameters from being added to a model. Existing methods also fail to provide objective and effective methods for determining when to terminate significance testing for scatterometry model optimization.

BRIEF DESCRIPTION OF THE DRAWINGS

The following description includes discussion of figures having illustrations given by way of example of implementations of embodiments of the invention. The drawings should be understood by way of example, and not by way of limitation.

DETAILED DESCRIPTION

Embodiments of the methods, apparatuses, and systems described herein may be used for optimizing optical parametric models employed in the practice of scatterometry. In an embodiment of the invention, a quantitative method for optimizing a parametric model includes objective significance testing to determine whether to include one or more parameters in a model. In one embodiment, the method prevents insignificant parameters from being added to the model by using statistical hypothesis testing that takes into account the outcome of previously tested parameters. For example, in one embodiment, the statistical hypothesis test takes into account whether previously tested parameters have passed the test and been included in the model. In one such embodiment, the statistical hypothesis test applies alpha spending or alpha investing rules. In one embodiment in which a plurality of parameters are tested for inclusion, the optical metrology system orders the parameters for testing according to some criteria. According to one embodiment, the optical metrology system sequentially includes and tests parameters until a stopping condition is reached. In one such embodiment, the stopping condition is reached when a number of consecutive parameters are rejected from the model. In embodiments of the invention, optimization methods can be performed whether the modeled data being fit is from a single site (e.g., at a wafer center), or from multiple sites (e.g., across one or more wafers).

As used herein, references to one or more "embodiments" are to be understood as describing a particular feature, structure, or characteristic included in at least one implementation of the invention. Thus, phrases such as "in one embodiment" or "in an alternate embodiment" appearing herein describe various embodiments and implementations of the invention, and do not necessarily all refer to the same embodiment. However, they are also not necessarily mutually exclusive. In the following description and claims, the term "coupled" and its derivatives may be used. The term "coupled" herein may refer to two or more elements which are in direct contact (physically, electrically, magnetically, optically, etc.), or to two or more elements that are not in direct contact with each other, but which still interact with each other.

In addition to various hardware components depicted in the figures and described herein, embodiments further include various operations which are described below. The operations described in accordance with such embodiments may be performed by hardware components or may be embodied in machine-executable instructions, which may be used to cause a general-purpose or special-purpose processor programmed with the instructions to perform the operations. Alternatively, the operations may be performed by a combination of hardware and software, including software instructions that perform the operations described herein via memory and one or more processors of a computing platform.

Figure 2A:
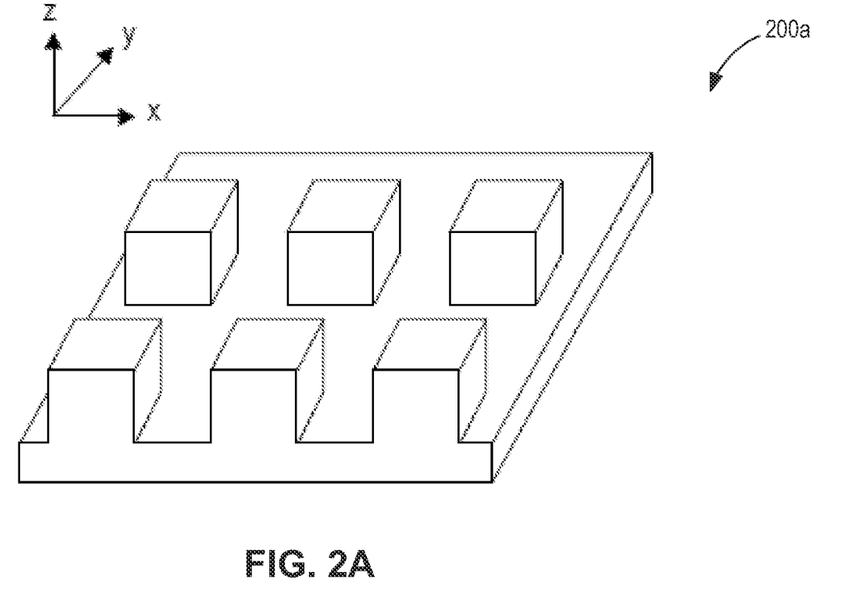
FIG. 2A illustrates a periodic grating having a profile that varies in the x-y plane, in accordance with an embodiment of the invention.
Figure 2B:
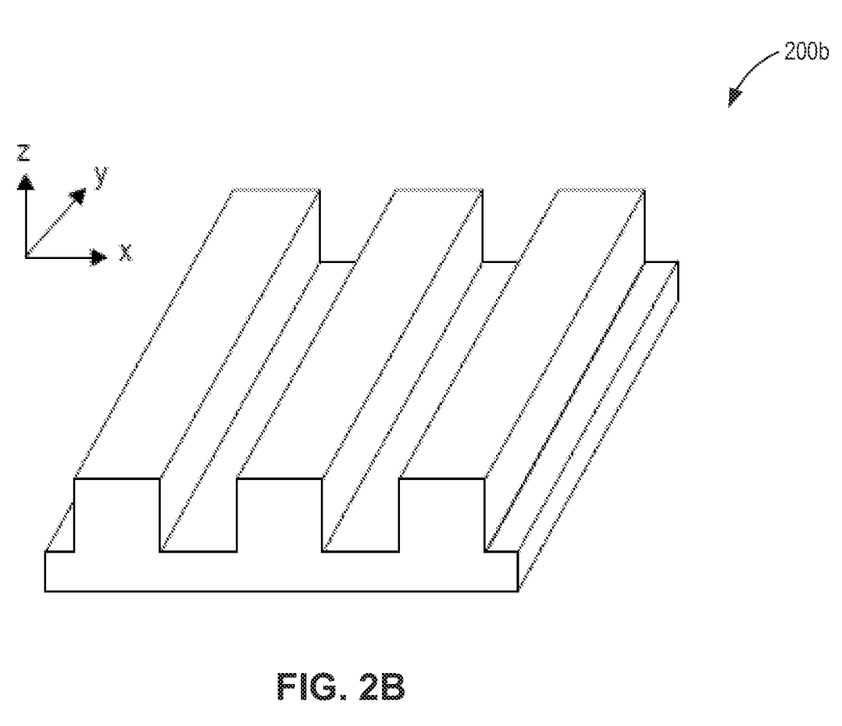
FIG. 2B illustrates a periodic grating having a profile that varies in the x-direction but not in the y-direction, in accordance with an embodiment of the invention.

FIGS. 2A and 2B are examples of diffracting structures which can be evaluated according to embodiments described herein. FIG. 2A illustrates an "island grating" 200a, which is periodic in two dimensions. The periodic grating 200a has a profile that varies in the x-y plane. The periodic grating 200a is also symmetric in two dimensions (here, in the x- and y-dimensions). A grating is symmetric in a dimension if the grating is the same on either side of a symmetry plane. For example, a grating is symmetric in the x-dimension if the grating is the same on either side of a plane defined by x=constant.

FIG. 2B illustrates a periodic grating having a profile that varies in the x-direction but not in the y-direction. Thus, periodic grating 200b is periodic in one dimension. It is to be understood that the lack of variation in the y-direction for a two-dimensional structure need not be infinite, but any breaks in the pattern are considered long range, e.g., any breaks in the pattern in the y-direction are spaced substantially further apart than the breaks in the pattern in the x-direction.

Figure 3:
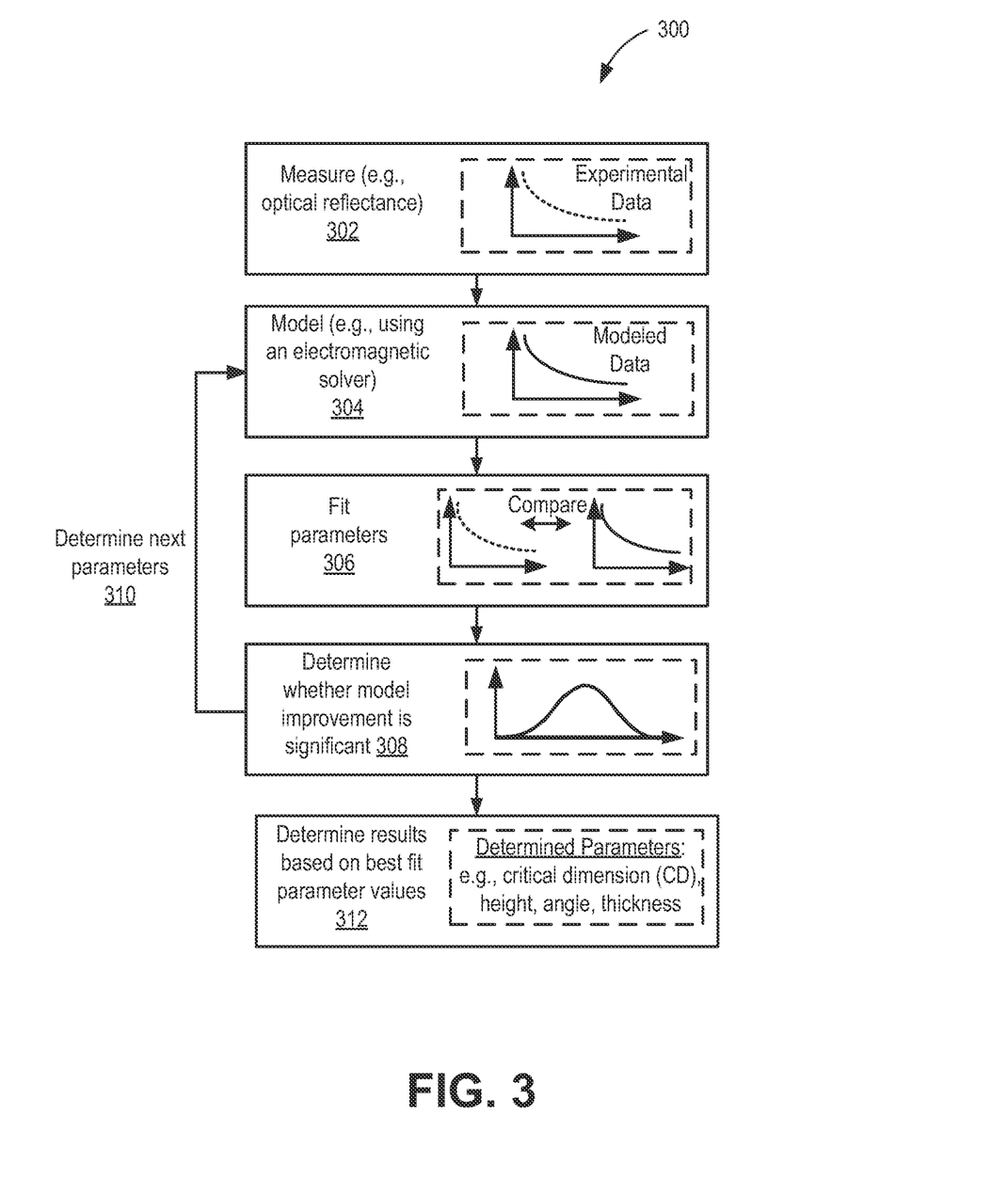
FIG. 3 illustrates a method for analyzing a diffracting structure, the method including parametric model optimization involving significance testing, in accordance with an embodiment of the invention.
Figure 4:
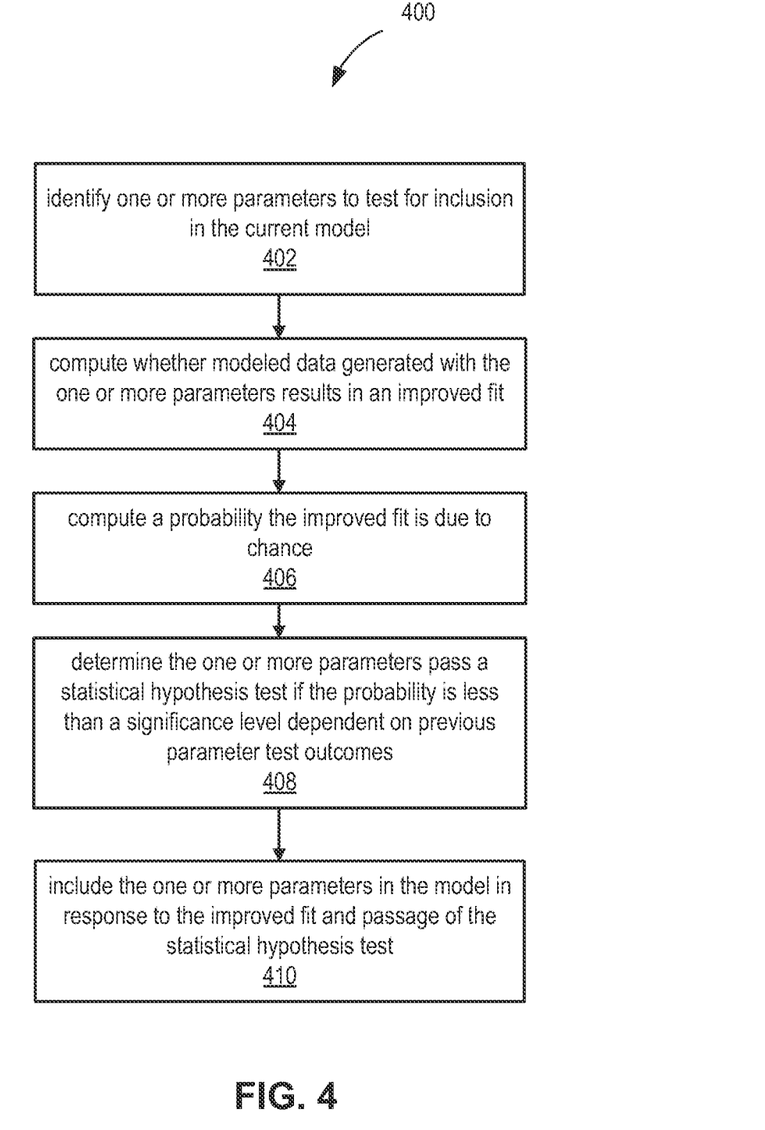
FIG. 4 illustrates a method of optimizing a model for evaluation of a diffracting structure, in accordance with an embodiment of the invention.
Figure 5:
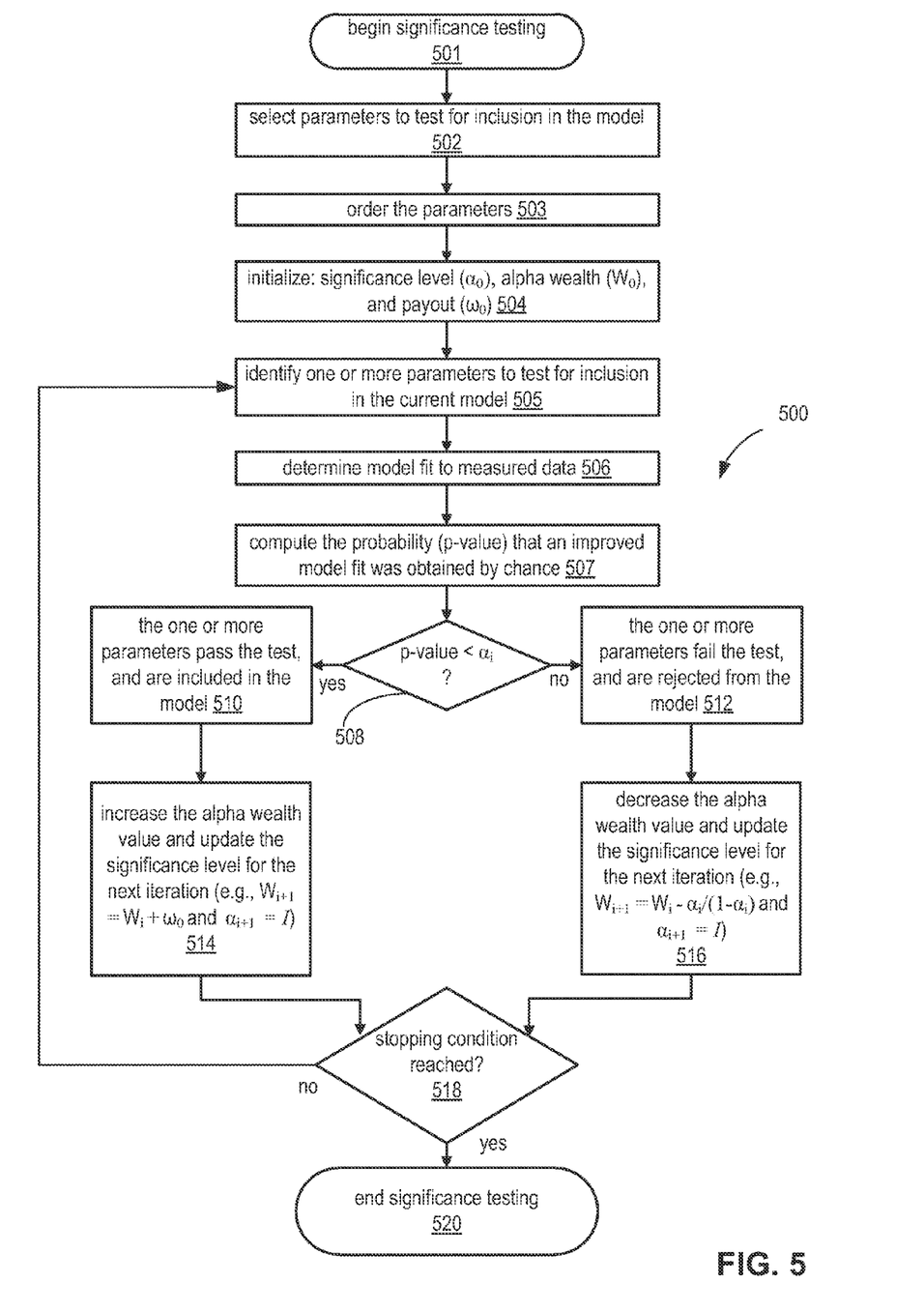
FIG. 5 illustrates a method of optimizing a model for evaluation of a diffracting structure, in accordance with an embodiment of the invention.

FIGS. 3-5 are flow diagrams illustrating exemplary methods for optimizing a model for evaluation of a diffracting structure, in accordance with embodiments of the invention. The following description refers to exemplary embodiments where the operations described in methods 300, 400, and 500 are computer implemented and executed as functions of an optical metrology system (e.g., the optical metrology system 704 of FIG. 7). However, the methods 300, 400, and 500 can be performed in whole or part by any appropriate computing system or combination of systems (e.g., the computing system 600 of FIG. 6, or any other computing system).

FIG. 3 illustrates a method 300 for analyzing a diffracting structure including parametric model optimizations involving significance testing, according to one embodiment of the invention. At block 302, an optical metrology system (e.g., the optical metrology system 100 of FIG. 1) performs measurements of a sample with a diffracting structure (e.g., the diffracting structures 200a of FIG. 2A or 200b of FIG. 2B). Performing measurements involves shining light on the sample and measuring spectral information for the sample. For example, the optical metrology system can illuminate the sample with a white light continuous spectrum and collect at a discrete number of wavelengths to obtain optical reflectance data. The optical metrology system can measure optical reflectance data at some or all of those wavelengths. Spectral data refers to reflectometric, ellipsometric data, or small angle x-ray scattering data, for example, as a function of wavelength, angle, or polarization. Spectral data can be represented as, for example, reflectance, tangent psi and cosine delta, alpha and beta, or Mueller matrix elements.

At block 304, the optical metrology system identifies an initial model of the measurement process. Identifying the initial model of the measurement process includes constructing a geometric model of the diffracting structure, determining how to parameterize the geometric model, characterizing the incident light, and characterizing the optical measurement system. Constructing the initial geometric model of the diffracting structure is generally based on nominal dimensional and material information provided by a user. Based on the model parameters, the optical metrology system computes modeled spectral data (e.g., via a simulation). For example, the optical metrology system can compute spectral data using rigorous diffraction modeling algorithms, such as the Rigorous Coupled Wave Analysis (RCWA) method based on Maxwell's equations.

At block 306, the optical metrology system attempts to fit the modeled data obtained at block 304 to the experimental data obtained at block 302. Fitting the modeled data generally involves comparing the modeled data to the experimental data and determining an error between the two sets of data. As indicated above, the initial model is generally based on nominal data that is typically insufficiently accurate to provide good fits of the model to the spectral data. Even if the user-provided information describes layer information well at the wafer center (where process variation is typically lower), the model is typically also used in scenarios with greater process variation, such as at the edge of the wafer, on other wafers, and other process lots. Therefore, the optical metrology system generally performs multiple iterations of model generation, simulation, and fitting modeled data to measured data at blocks 304 and 306.

At each model iteration, the optical metrology system can include or exclude different parameters from the model in order to improve the model fit to the measured data. Including a parameter involves "floating" the parameter (i.e., computing model data with the parameter as a variable). Excluding a parameter can involve fixing the parameter at a constant value. Excluding a parameter can also involve computing model data without the parameter. To determine whether to include or exclude a parameter, in one embodiment the optical metrology system determines whether any improvement in fit is statistically significant at block 308. In one embodiment, the optical metrology system performs statistical hypothesis testing to objectively determine which parameters to include in the model. In one such embodiment, the statistical hypothesis testing involves alpha spending or alpha investing rules. As is explained in further detail below, alpha spending and alpha investing rules take into consideration whether previous parameters passed the statistical hypothesis test, according to one embodiment. In one embodiment, prior to testing parameters for inclusion in the model, the optical metrology system orders the parameters to test according to some criteria.

The optical metrology system repeats blocks 304-310 until one or more conditions occur indicating the regression should be terminated. For example, in one embodiment, the optical metrology system terminates testing when a number of parameters have been rejected from the model.

Once a condition is reached for terminating the regression, the optical metrology system can determine values of parameters of the actual diffracting structure based on the best fit model parameters, at block 312. Upon completing the regression, the scatterometry model is typically close enough to the actual diffracting structure that characterizing the actual diffracting structure may simply involve ascertaining the best fit model parameters. This can be true, for example, for geometric parameters that have a one-to-one correspondence with a single parameter used in the scatterometry model. Determining other properties or attributes of the actual diffracting structure may involve additional operations such as adding two parameters of the scatterometry model together.

Method 400 of FIG. 4 illustrates one embodiment for optimizing a model for evaluation of a diffracting structure, the method including objective techniques for determining whether to include parameters in the model. Method 400 begins with the optical metrology system identifying one or more parameters to test for inclusion in the current model at block 402. Parameters can include dimensional parameters, material parameters, geometric parameters, principle component parameters, a linear combination of parameters, or any other parameters used for characterizing a diffracting structure and/or a process. Dimensional parameters can include, for example, CDs, HTs, and film thicknesses. Geometric parameters can include, for example, SWAs and unit cell orthogonality angle. Material parameters can include, for example, dielectric constants. Principle component parameters can include, for example, a linear combination of variables in the model.

Next, the optical metrology system computes whether modeled data generated with the one or more parameters results in an improved fit at block 404. For example, in one embodiment, the optical metrology system computes a difference between modeled data generated with the one or more parameters and measured data for the diffracting structure. The optical metrology system determines whether there is a reduction or increase in the difference between the modeled data and the measured data as compared to previous modeled data generated without the one or more parameters. If the difference between the modeled data and measured data is smaller compared to previously modeled data, the changes to the model improve the model fit. At block 406, the optical metrology system computes a probability the improved fit is due to chance.

Method 400 concludes with the optical metrology system including the one or more parameters in the model in response to an improved fit and passage of a statistical hypothesis test at block 406. In one such embodiment, the parameters pass the statistical hypothesis test if the improved fit is less than a significance level. In one embodiment, the significance level is dependent upon previous parameter test outcomes. For example, the significance level can be based on whether one or more previously tested parameters were included in the model. In one such embodiment, the statistical hypothesis test can be based on alpha spending or alpha investing rules, as described below in more detail with reference to FIG. 5.

Method 500 of FIG. 5 illustrates optimizing a model for evaluation of a diffracting structure, including statistical hypothesis testing based on alpha investing, according to one embodiment. Method 500 begins at block 501, and with the optical metrology system selecting parameters to test for inclusion in the model at block 502. The parameters selected for inclusion in the model can include all the parameters in the model, or a subset of parameters. For example, the parameters to be tested for inclusion in the model can include a subset of parameters known to significantly affect model fitting. Selection of parameters to test for inclusion can be made by a user, or by the optical metrology system (e.g., randomly, or based on a function which, for example, relies on previous user input or collected data). In one embodiment, the optical metrology system includes and tests parameters sequentially. For example, in one embodiment, one or more of the selected parameters is included in each model iteration. A model iteration can include, for example, operations in blocks 304-310 of FIG. 3.

If the optical metrology system selects more than one parameter to test for inclusion in the model, in one embodiment, the optical metrology system orders the parameters according to one or more criteria at block 503. Ordering of parameters can be performed by the user, the optical metrology system, or by a combination of the optical metrology system with user input. For example, the user can supply the criteria for ordering the parameters, and the optical metrology system can perform the ordering. In another example, the user supplies the parameters pre-ordered. In yet another example, the optical metrology system orders the parameters based on criteria not directly supplied by the user (e.g., based on criteria derived from previous simulations). In one embodiment, the optical metrology system orders the parameters according to sensitivity (i.e., signal-to-noise ratio), correlation amongst the parameters, precision, a combination thereof, or according to any other appropriate scatterometry model criteria. Parameters with high sensitivity result in a larger improvement to the model fit quality for the same common model change than parameters with low sensitivity (e.g., high sensitivity parameters can reduce chi-square faster than low sensitivity parameters). In one embodiment, the optical metrology system orders parameters such that high sensitivity parameters are tested for inclusion prior to lower sensitivity parameters. Parameters are considered correlated if a change to a modeled diffraction signal due to a change in a first parameter is similar to the change in the diffraction signal due to a change in a second parameter. In one embodiment, the optical metrology system orders parameters such that parameters with lower correlation are tested for inclusion prior to parameters with higher correlation. Parameter precision is related to the noise level of the measurement; repeated measurement of a high precision parameter results in a low standard deviation. In one embodiment, the optical metrology system orders parameters such that higher precision parameters are tested for inclusion prior to lower precision parameters. Ordering the parameters to test for inclusion can also involve nested ordering, where parameters with the same or similar values for one criteria are ordered according to one or more additional criteria. For example, in one embodiment, if two or more parameters have similar or identical sensitivity, those parameters having similar or identical sensitivity can also be ordered based on correlation. Other combinations of nested ordering are possible. In other embodiments, the parameters selected for inclusion in the model are not ordered according to particular criteria.

Prior to testing parameters for inclusion in the model, the optical metrology system initializes variables to be used in the testing. For example, in one embodiment the optical metrology system initializes: a significance "alpha" level ($\alpha_0$), an alpha wealth value ($W_0$), and a payout value ($\omega_0$) at block 504. The optical metrology system uses the significance level to determine whether a model improvement is statistically significant, and, if so, decide to include the corresponding parameter in the model. According to one embodiment, the significance level is at or below a maximum acceptable "false discovery rate" (FDR), where a "discovery" is a finding, through a suitable statistical test, that a parameter should be added to a model. The FDR is generally a ratio of the number of falsely added parameters (e.g., the number of added noise parameters) to the total number of added parameters, and may therefore provide one measure of model quality. Thus, according to one embodiment where the optical metrology system is to test for significance N parameters in the model, the significance level is set to 1/N. In one such embodiment, setting the initial significance level to 1/N guards against the addition of even one noise parameter to the model. If, by experience, the user knows that a large number of failed significance tests typically occur after testing approximately the first X parameters, then in another embodiment the significance level can be set to 1/X. In one embodiment, the optical metrology system sets the initial significance level to 0.05. According to one embodiment, the optical metrology system initializes the alpha wealth value and/or the payout value to the initial significance level. The use of the alpha wealth value, $W_0$, and payout value, $\omega_0$, are described in greater detail below.

After selecting the parameters to test for inclusion and initializing variables for the testing, the optical metrology system begins by identifying one or more parameters to test for inclusion in the current model at block 505. If the optical metrology system ordered the selected parameters, then the testing begins by including the first of the ordered parameters. As indicated above, parameters can be added one at a time or in groups. For example, the optical metrology system can add the primary dispersion parameters for a polysilicon layer to the current model at one time, thereby testing the significance of polysilicon n,k variation all at once.

The optical metrology system determines the model fit to the measured data obtained with the one or more new parameters at block 506. Determining the model fit to the measured data can include determining the chi-square change due to the model change. Next, in one embodiment, the optical metrology system assesses the significance of the chi-square change due to adding the one or more parameters by computing the F-statistic and the probability (p-value) that an improved model fit was obtained by chance at block 507. In one such embodiment, the optical metrology system estimates whether a chi-square change obtained by changing the model is statistically significant. In certain embodiments, this can begin by stating a so-called "null hypothesis" to disprove. The "null hypothesis" can be stated as: "The chi-square change obtained by modifying the model (through inclusion or exclusion of one or more model parameters) could be obtained merely by chance." In certain embodiments, if a statistical test rejects the null hypothesis, then the chi-square change obtained by adding a parameter is significant and the model change is justified. For example, the optical metrology system computes the probability of obtaining the observed improved fit by applying an F-test. By applying the F-test, the optical metrology system computes an F-statistic based on the chi-square change of the modeled data obtained by including the one or more parameters. The F-statistic is based on random variables, and therefore is a probability distribution. In one embodiment, the optical metrology system can use the F-distribution to compute the probability that a given chi-square improvement can take place randomly. In one such embodiment, the F-distribution is a scaled ratio of chi-square distributed variables. According to one embodiment, the F-statistic is based on a ratio of the number of degrees of freedom in the model and a number of parameters in the model, as is illustrated in equation (1). In equation (1), F is the F-statistic, $\Delta\chi^2$ is the chi-square change obtained by adding $d_1$ parameters to the model and refitting, $d_2$ is the number of degrees of freedom in the current model, and $\chi_0^2$ is the model fit chi-square for the current model:

$$F = \frac{d_2}{d_1} \frac{\Delta\chi^2}{\chi_0^2} \qquad (1)$$

According to one embodiment, the number of degrees of freedom, $d_2$, is given by equation (2). In equation (2), NWL is the number of model wavelengths (or the number of angles for angle-based data) used in the model, and N is the current number of parameters in the model:

$$d_2 = NWL - N \qquad (2)$$

When testing parameters for inclusion in the model, the value of $d_1$ can be one or more. In a stepwise model optimization in which parameters are added and tested one at a time, $d_1=1$. The optical metrology system can then compute a "p-value" using the statistic (e.g., F-statistic), which indicates the probability that this statistic could have been obtained merely by chance.

After determining the p-value, the optical metrology system determines whether the p-value is less than the significance level at block 508. If the p-value is less than the significance level, $\alpha_i$, the optical metrology system determines that the one or more parameters pass the test and includes the parameters in the model at block 510. If the p-value is greater than or equal to the significance level, the optical metrology system determines that the one or more parameters fail the test, and rejects (i.e., excludes) the parameters from the model at block 512.

Some methods of significance testing require the p-values of all significance tests to be available simultaneously for comparison (see, e.g., Benjamini, Yoav et al., "Controlling the False Discovery Rate: A Practical and Powerful Approach to Multiple Testing," Journal of the Royal Statistical Society, Series B (Methodological), Vol. 57, No. 1 (1995), pages 289-300). Such methods can be inconvenient for optical model optimization because the user may not be able to foresee the set of models that will be tested over the course of an optimization project. According to one embodiment, the optical metrology system dynamically adjusts the significance level as new significance tests are performed and does not require p-values of all significance tests to be available simultaneously, while at the same time controlling FDR at some given level. Such embodiments can involve, for example, "alpha spending" or "alpha investing" (see, e.g., Foster, Dean P., et al., "Alpha-investing: A procedure for sequential control of expected false discoveries," Department of Statistics, The Wharton School of the University of Pennsylvania, Jul. 24, 2007).

In methods employing alpha spending or alpha investing, an initial "alpha wealth value" is specified. In one embodiment, once the alpha wealth is reduced to zero or another threshold value, no further model tests are performed. According to one embodiment using alpha spending, each test at a significance level a, reduces the alpha wealth. A method employing alpha spending implements a Bonferroni rule, and therefore can be considered a more conservative method. In embodiments involving alpha investing, the optical metrology system modifies the alpha wealth value based on whether the one or more parameters pass or fail the test, and updates the significance level for the next iteration at blocks 514 or 516. For example, the alpha wealth is increased upon a successful test (e.g., a discovery, or rejection of the null hypothesis), and decreased if the test is unsuccessful. In one such example, if the one or more parameters pass the significance test, the optical metrology system increases the alpha wealth value by the payout value, as is illustrated in equation (3), where $W_i$ is the current alpha wealth level, $W_{i+1}$ is the alpha wealth level to be used in the next iteration, and $\omega_0$ is the payout:

$$W_{i+1} = W_i \omega_0 \qquad (3)$$

As mentioned above, in one embodiment, the payout is set to the initial significance level. If the parameters fail the test, the optical metrology system decreases the alpha wealth value for the next iteration at block 516. For example, the optical metrology system decreases the alpha wealth value by the current significance level divided by one minus the current significance level, as illustrated in equation (4):

$$W_{i+1} = W_i - \frac{\alpha_i}{1 - \alpha_i} \qquad (4)$$

The optical metrology system also updates the significance level at blocks 514 or 516. The significance level can be a function of, for example, an alpha investing rule, I, as illustrated in equation (5):

$$\alpha_{i+1} = I \qquad (5)$$

The optical metrology system can apply one or more alpha investing rules for model optimization. In one embodiment, an alpha investing rule is a function of the alpha wealth level. For example, the alpha investing rule can be applied such that the significance level is equal to the alpha wealth value multiplied by a current iteration number minus one, divided by one plus the current iteration number minus a most recent iteration in which a parameter was excluded from the model, as illustrated in equation (6). In equation (6), k is the most recent iteration in which one or more parameters were rejected:

$$I = \frac{W(i-1)}{1+i-k} \qquad (6)$$

In one embodiment, the FDR is controlled approximately at the significance level, $\alpha_0$, if the initial alpha wealth $W_0$ is approximately less than or equal to $\alpha_0$, the payout is approximately less than or equal to $\alpha_0$, and the alpha wealth decreases according to equation (4) above. According to one embodiment, optimization methods employing alpha investing have more statistical power than alpha spending (greater power to reject the null hypothesis when it is false), provide uniform control of FDR (e.g., controls FDR at any stage of the testing sequence), and allow for the incorporation of domain knowledge in designing the testing sequence. Thus, in methods employing alpha investing, a user can choose parameters that are known to be significant for the beginning of the test sequence and buy additional wealth for subsequent tests of parameters with low significance or model sensitivity. An ordering of the parameters such that significant parameters are tested first can also enhance the user's ability to optimize the model for low sensitivity parameters without adding excessive noise parameters.

Next, at block 518 the optical metrology system determines whether a stopping condition is reached. A stopping condition can include, for example, reaching a threshold number of consecutively excluded parameters. In one such example, the optical metrology system terminates the testing upon consecutively excluding three parameters. Other embodiments can terminate testing upon reaching other numbers of consecutively excluded parameters, for example, two parameters, or greater than three parameters. A certain number of consecutive parameters being rejected for addition to the model could indicate that a floor in chi-square has been encountered from some systematic error source, and that subsequent significance tests will fail. The user can provide input regarding the number of consecutive test failures that will trigger termination of significance testing, or the optical metrology system can collect data and identify such termination conditions. Other stopping conditions can include: reaching (or sufficiently approaching) convergence such that the model error is below a threshold value, reaching a maximum number of iterations, and/or any other conditions justifying discontinuing further model iterations.

If a stopping condition is reached, the optical metrology system ends the significance testing at block 520. If a stopping condition is not reached, the optical metrology system repeats the statistical hypothesis test for additional parameters until a stopping condition is reached, for example, by identifying the next one or more parameters to test for inclusion in the next model at block 505.

Figure 6:
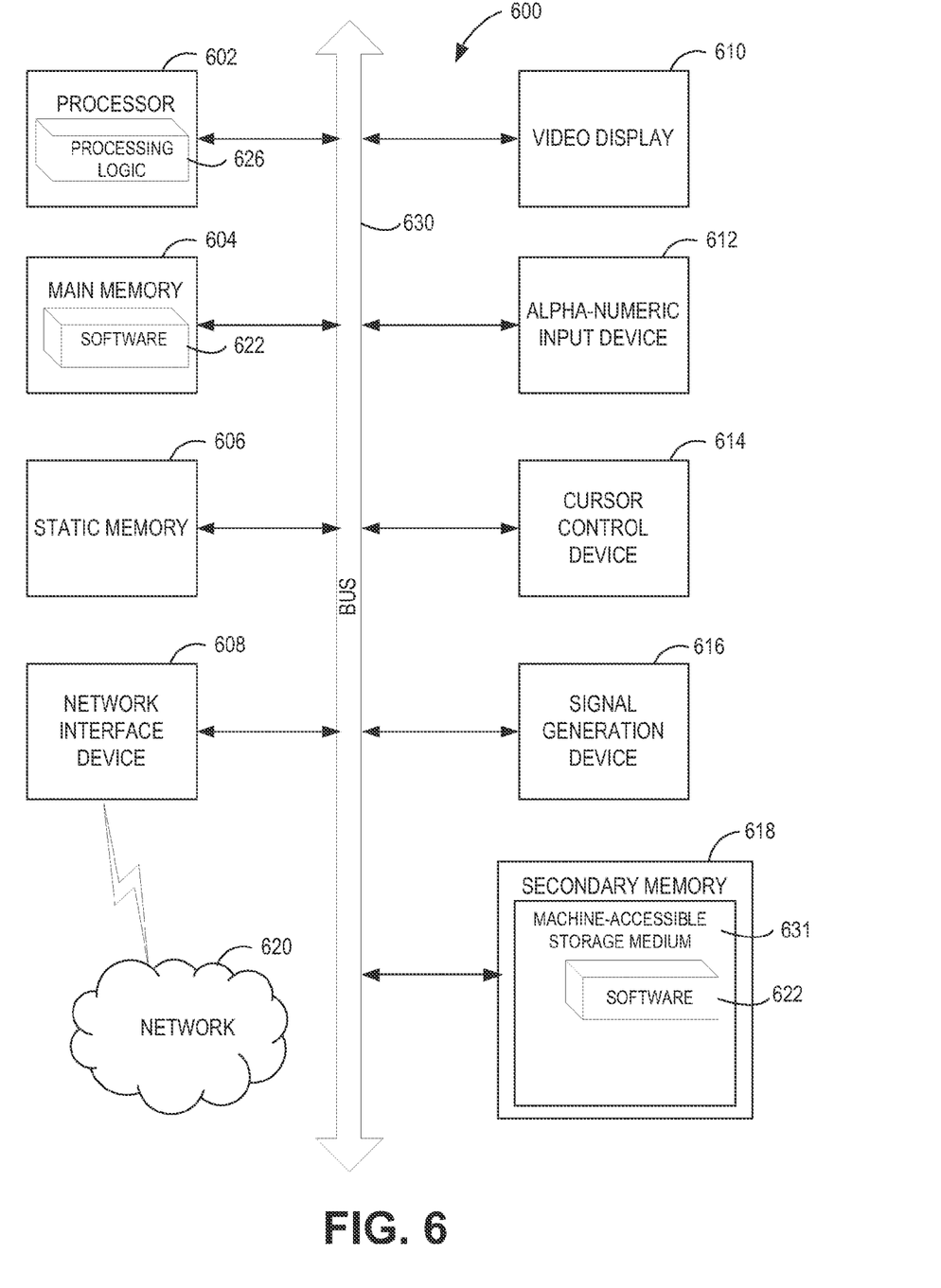
FIG. 6 illustrates a block diagram of an exemplary computing system in accordance with which embodiments may operate, be installed, integrated, or configured.

In addition to the methods described with reference to FIGS. 3-5, embodiments also relate to a system or apparatus for performing the operations herein. The disclosed system or apparatus may be specially constructed for the required purposes, or it may comprise a general purpose computer selectively activated or reconfigured by a computer program stored in the computer or accessed through cloud storage. For example, FIG. 6 illustrates a block diagram of an exemplary computing system in accordance with which embodiments may operate, execute, be installed, integrated, or configured. According to one embodiment, the computing system 600 can output, to a display or a physical storage medium, an estimate of one or more physical attributes of a diffracting structure based on a stored model. In embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a server, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computing system 600 includes a processor 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a secondary memory 618 (e.g., a data storage device), which communicate with each other via a bus 630.

Processor 602 represents one or more general-purpose processing devices such as a microprocessor, central processing unit, or the like. More particularly, the processor 602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 602 may also be one or more special-purpose processing devices such as an application specific integrated circuit (ASIC), a field programmable gate array (FPGA), a digital signal processor (DSP), network processor, or the like. Processor 602 is configured to execute the processing logic 626 for performing the operations and steps discussed herein.

The computing system 600 may further include a network interface device 608. The computing system 600 also may include a video display unit 610 (e.g., a liquid crystal display (LCD) or a cathode ray tube (CRT)), an alpha-numeric input device 612 (e.g., a keyboard), a cursor control device 614 (e.g., a mouse), and a signal generation device 616 (e.g., a speaker).

The secondary memory 618 may include a machine-accessible storage medium (or more specifically a computer-readable storage medium) 631 on which is stored one or more sets of instructions (e.g., software 622) embodying any one or more of the methodologies or functions described herein. For example, in one embodiment, a machine-readable storage medium has instructions stored thereon which, when executed by a data processing system, cause the data processing system to perform a method of optimizing a model for evaluation of a diffracting structure, the method including: identifying one or more parameters to test for inclusion in the model. The method includes computing whether modeled optical reflectance data generated with the one or more parameters results in an improved fit to measured optical reflectance data collected from the diffracting structure over previous modeled data generated without the one or more parameters. The method includes computing a probability that the improved fit is due to chance, and determining the one or more parameters pass a statistical hypothesis test in response to the probability being less than a significance level dependent on whether one or more previously tested parameters passed the statistical hypothesis test. The method also includes storing to an electronic memory the one or more parameters as part of the model in response to the improved fit and passage of the statistical hypothesis test by the one or more parameters.

The software 622 may also reside, completely or at least partially, within the main memory 604 and/or within the processor 602 during execution thereof by the computing system 600, the main memory 604 and the processor 602 also constituting machine-readable storage media. The software 622 may further be transmitted or received over a network 620 via the network interface device 608.

While the machine-accessible storage medium 631 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, any type of disk including floppy disks, optical disks, flash, NAND, solid state drives (SSDs), CD-ROMs, magnetic-optical disks, read-only memories (ROMs), random access memories (RAMs), EPROMs, EEPROMs, magnetic or optical cards, or any similar type of non-transitory media suitable for storing electronic instructions on a time scale that is sufficient to be considered non-transitory by one of ordinary skill in the art. In one embodiment, a non-transitory computer readable storage medium having instructions stored thereon, causes one or more processors within a scatterometry measurement apparatus to perform the methods and operations described herein. In another embodiment, the instructions to perform such methods and operations are stored upon a non-transitory computer readable medium for later execution.

Figure 7:
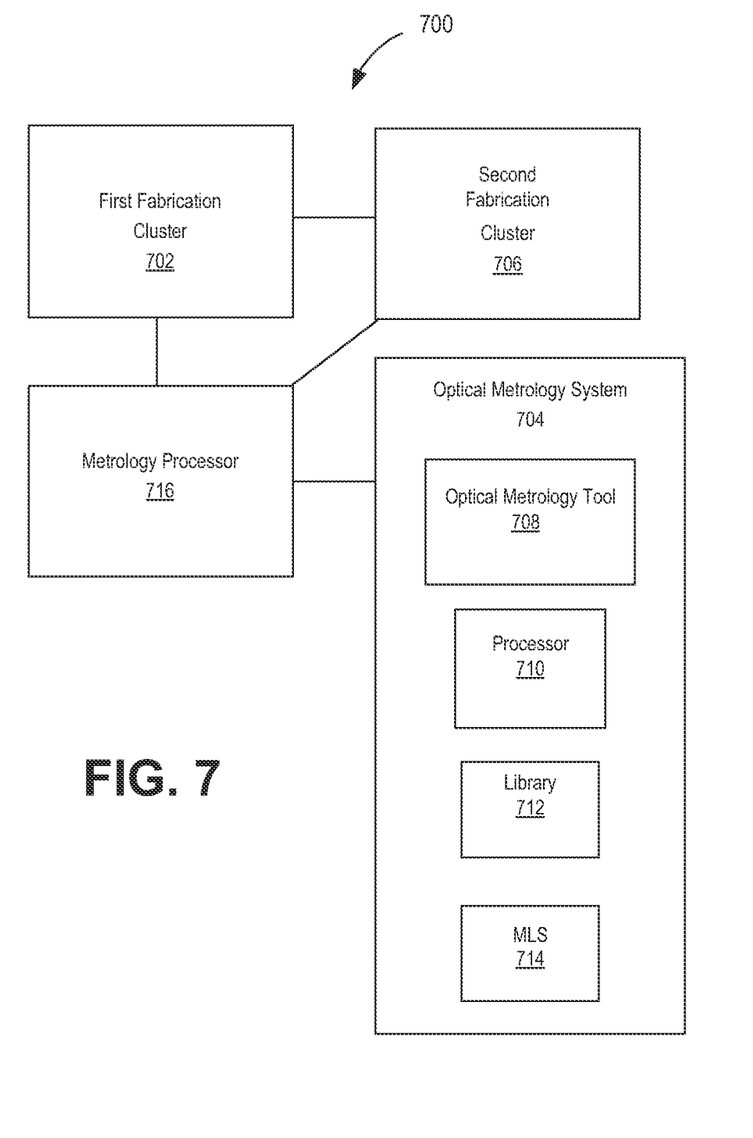
FIG. 7 is a block diagram illustrating select elements of a system according to an embodiment for determining and utilizing profile parameters for automated process and equipment control.

FIG. 7 is an exemplary block diagram of a system for determining and utilizing profile parameters for automated process and equipment control.

System 700 includes a first fabrication cluster 702 and an optical metrology system 704 (e.g., an optical measurement system). The optical metrology system 704 can include, for example, a spectroscopic ellipsometer (SE), a dual-beam spectrophotometer (DBS), a polarized DBS, a beam reflectometer, or any other optical measurement system. System 700 also includes a second fabrication cluster 706. Although the second fabrication cluster 706 is depicted in FIG. 7 as being subsequent to the first fabrication cluster 702, it should be recognized that the second fabrication cluster 706 can be located prior to the first fabrication cluster 702 in the system 700 (e.g., and in the manufacturing process flow).

A photolithographic process, such as exposing and/or developing a photoresist layer applied to a wafer, can be performed using the first fabrication cluster 702. In one exemplary embodiment, the optical metrology system 704 includes an optical metrology tool 708 and a processor 710. The optical metrology tool 708 is configured to measure a diffraction signal off of the structure. If the measured diffraction signal and the simulated diffraction signal match, one or more values of the profile parameters are presumed equal to the one or more values of the profile parameters associated with the simulated diffraction signal.

In one exemplary embodiment, the optical metrology system 704 can also include a library 712 with a plurality of simulated (e.g., computed) diffraction signals and a plurality of values of one or more profile parameters associated with the plurality of simulated diffraction signals. The library can be generated in advance. The processor 710 can compare a measured diffraction signal of a structure to the plurality of simulated diffraction signals in the library. When a matching simulated diffraction signal is found, the one or more values of the profile parameters associated with the matching simulated diffraction signal in the library is assumed to be the one or more values of the profile parameters used in the wafer application to fabricate the structure.

The system 700 also includes a metrology processor 716. In one exemplary embodiment, the processor 710 can transmit the one or more values of the one or more profile parameters to the metrology processor 716. The metrology processor 716 can then adjust one or more process parameters or equipment settings of the first fabrication cluster 702 based on the one or more values of the one or more profile parameters determined using the optical metrology system 704. The metrology processor 716 can also adjust one or more process parameters or equipment settings of the second fabrication cluster 706 based on the one or more values of the one or more profile parameters determined using the optical metrology system 704. As noted above, the second fabrication cluster 706 can process the wafer before or after the first fabrication cluster 702. In another exemplary embodiment, the processor 710 is configured to train a machine learning system 714 using the set of measured diffraction signals as inputs to the machine learning system 714 and profile parameters as the expected outputs of the machine learning system 714.

One or more components of the system 700 can include or implement embodiments of the invention as described herein in the context of methods 300, 400, and 500. For example, in one embodiment the optical metrology system 704 includes logic for receiving optical reflectance measurements for the diffracting structure. Logic for receiving measurements can be included in, for example, the optical metrology tool 708. A processor (e.g., the processor 710) can be configured to optimize a model for evaluation of a diffracting structure, the method including: identifying one or more parameters to test for inclusion in the model, computing a difference between modeled data generated with the one or more parameters and measured data for the diffracting structure, including the one or more parameters in the model in response to a reduction in the difference between the modeled data and the measured data compared to previous modeled data generated without the one or more parameters, and passing a statistical hypothesis test based on whether one or more previously tested parameters were included in the model. In further embodiments, any and/or all of the statistical techniques described in method 500 may be performed by the processor (e.g., 710).

Thus, a method of parametric model optimization is described. The probability of adding a noise parameter can be controlled to a user settable level. In one embodiment, the method is automatable through programmatic control of computerized system hardware, which can enable a higher degree of consistency in model optimization between one user and another.

Besides what is described herein, various modifications can be made to the disclosed embodiments and implementations of the invention without departing from their scope. Therefore, the illustrations and examples herein should be construed in an illustrative, and not a restrictive sense. The scope of the invention should be measured solely by reference to the claims that follow.

I claim:

1. A computer implemented method for evaluation of a diffracting structure, the method comprising:
    performing measurements of the diffracting structure with a detector of an optical metrology system, including measuring optical reflectance of the diffracting structure;
    identifying one or more parameters to test for inclusion in the model of the diffracting structure;
    computing whether modeled optical reflectance data generated with the one or more parameters results in an improved fit to the measured optical reflectance data collected from the diffracting structure over previous modeled data generated without the one or more parameters;
    computing a probability that the improved fit is due to chance;
    determining the one or more parameters pass a statistical hypothesis test in response to the probability being less than a significance level dependent on whether one or more previously tested parameters passed the statistical hypothesis test;

storing to an electronic memory the one or more parameters as part of the model in response to the improved fit and passage of the statistical hypothesis test by the one or more parameters; and determining a value of one or more parameters of the diffracting structure using the stored model.

2. The method of claim 1, wherein determining a value of one or more parameters of the diffracting structure using the stored model includes:

performing a computation of at least one physical characteristic of the diffracting structure based on the measured optical reflectance data using the stored model.

3. The method of claim 2, wherein computing the probability comprises:

computing an F-statistic based on a chi-square change of the modeled optical reflectance data obtained by including the one or more parameters, wherein the F-statistic is based on a ratio of the number of degrees of freedom in the model and a number of parameters in the model.

4. The method of claim 1, further comprising:

setting an initial significance level;

setting an alpha wealth value to the initial significance level, wherein the statistical hypothesis testing terminates in response to the alpha wealth value decreasing to a threshold value;

decreasing the alpha wealth value by a first amount in response to the passage, by the one or more previously tested parameters, of the statistical hypothesis test;

increasing the alpha wealth value by a second amount in response to the passage, by the one or more previously tested parameters, of the statistical hypothesis test; and modifying the significance level based on the increased or decreased alpha wealth value.

5. The method of claim 4, wherein:

the first amount is given by a current significance level divided by one minus the current significance level;

the second amount is the initial significance level; and the current significance level is set to the alpha wealth value multiplied by a current iteration number minus one, divided by one plus the current iteration number minus a most recent iteration in which a parameter failed the statistical hypothesis test.

6. The method of claim 1, wherein the one or more parameters comprise a plurality of parameters, the method further comprising:

ordering the plurality of parameters for testing according to sensitivity, wherein high sensitivity parameters are to be tested prior to low sensitivity parameters; and sequentially including and testing the plurality of parameters with the statistical hypothesis test.

7. The method of claim 1, wherein the one or more parameters comprise a plurality of parameters, the method further comprising:

ordering the plurality of parameters for testing according to correlation, wherein low correlation parameters are to be tested prior to high correlation parameters; and sequentially including and testing the plurality of parameters with the statistical hypothesis test.

8. The method of claim 1, wherein the one or more parameters comprise a plurality of parameters, the method further comprising:

ordering the plurality of parameters for testing first according to sensitivity, wherein high sensitivity parameters are to be tested prior to low sensitivity parameters;

ordering the parameters having a same sensitivity according to correlation, wherein low correlation parameters are to be tested prior to high correlation parameters; and sequentially including and testing the plurality of parameters with the statistical hypothesis test.

9. The method of claim 1, wherein the one or more parameters comprise a plurality of parameters, the method further comprising:

ordering the plurality of parameters for testing according to precision, wherein high precision parameters are to be tested prior to low precision parameters; and sequentially including and testing the plurality of parameters with the statistical hypothesis test.

10. The method of claim 1, further comprising:

repeating the statistical hypothesis test for additional parameters until a stopping condition is reached, wherein the stopping condition comprises reaching a number of consecutively excluded parameters.

11. The method of claim 10, further comprising:

ordering the plurality of parameters for testing according to sensitivity;

wherein the number of consecutively excluded parameters that result in the stopping condition being reached is three or greater.

12. A machine-readable storage medium having instructions stored thereon which, when executed by a data processing system, cause the data processing system to perform a method of optimizing a model for evaluation of a diffracting structure, the method comprising:

performing measurements of the diffracting structure with a detector of an optical metrology system, including measuring optical reflectance of the diffracting structure;

identifying one or more parameters to test for inclusion in the model of the diffracting structure;

computing whether modeled optical reflectance data generated with the one or more parameters results in an improved fit to the measured optical reflectance data collected from the diffracting structure over previous modeled data generated without the one or more parameters;

computing a probability that the improved fit is due to chance;

determining the one or more parameters pass a statistical hypothesis test in response to the probability being less than a significance level dependent on whether one or more previously tested parameters passed the statistical hypothesis test;

storing to an electronic memory the one or more parameters as part of the model in response to the improved fit and passage of the statistical hypothesis test by the one or more parameters; and determining a value of one or more parameters of the diffracting structure based on the stored model.

13. The machine-readable storage medium of claim 12 having instructions stored thereon which, when executed by a data processing system, cause the data processing system to perform the method further comprising:

setting an initial significance level;

setting an alpha wealth value to the initial significance level, wherein the statistical hypothesis testing terminates in response to the alpha wealth value decreasing to a threshold value;

decreasing the alpha wealth value by a first amount in response to the passage, by the one or more previously tested parameters, of the statistical hypothesis test;

increasing the alpha wealth value by a second amount in response to the passage, by the one or more previously tested parameters, of the statistical hypothesis test; and modifying the significance level based on the increased or decreased alpha wealth value.

14. The machine-readable storage medium of claim 12 having instructions stored thereon which, when executed by a data processing system, cause the data processing system to perform the method further comprising:

ordering the plurality of parameters for testing according to sensitivity, wherein high sensitivity parameters are to be tested prior to low sensitivity parameters; and sequentially including and testing the plurality of parameters with the statistical hypothesis test.

15. The machine-readable storage medium of claim 12, further comprising:

repeating the statistical hypothesis test for additional parameters until a stopping condition is reached, wherein the stopping condition comprises reaching a number of consecutively excluded parameters.

16. An optical measurement system comprising:

a scatterometry tool including a detector for performing optical measurements of a diffracting structure disposed on a sample, performing optical measurements including the scatterometry tool to generate optical reflectance measurement data for the diffracting structure;

first logic for receiving the optical reflectance measurement data for the diffracting structure;

an electronic memory to store a model for evaluation of the diffracting structure;

a processor to:

optimize the model for evaluation of the diffracting structure according to a method comprising:

identifying one or more parameters to test for inclusion in the model;

computing whether modeled optical reflectance data generated with the one or more parameters results in an improved fit to the optical reflectance measurement data over previous modeled data generated without the one or more parameters;

computing a probability that the improved fit is due to chance;

determining the one or more parameters pass a statistical hypothesis test in response to the probability being less than a significance level dependent on whether one or more previously tested parameters passed the statistical hypothesis test;

storing to the electronic memory the one or more parameters as part of the model in response to the improved fit and passage of the statistical hypothesis test by the one or more parameters; and determining a value of one or more parameters of the diffracting structure using the stored model.

17. The optical measurement system of claim 16, wherein determining a value of one or more parameters of the diffracting structure using the stored model includes:

performing a computation of at least one physical characteristic of the diffracting structure based on the measured optical reflectance data using the stored model.

18. The optical measurement system of claim 16, the optical measurement system further comprising:

a display to display the modeled optical reflectance data; and second logic to output the modeled optical reflectance data to the display.

19. The optical measurement system of claim 16, the processor to optimize the model for evaluation of the diffracting structure according to the method further comprising:

setting an initial significance level;

setting an alpha wealth value to the initial significance level, wherein the statistical hypothesis testing terminates in response to the alpha wealth value decreasing to a threshold value;

decreasing the alpha wealth value by a first amount in response to the passage, by the one or more previously tested parameters, of the statistical hypothesis test;

increasing the alpha wealth value by a second amount in response to the passage, by the one or more previously tested parameters, of the statistical hypothesis test; and modifying the significance level based on the increased or decreased alpha wealth value.

20. The optical measurement system of claim 16, the processor to optimize the model for evaluation of the diffracting structure according to the method further comprising:

ordering the plurality of parameters for testing according to sensitivity, wherein high sensitivity parameters are to be tested prior to low sensitivity parameters; and sequentially including and testing the plurality of parameters with the statistical hypothesis test.

21. The machine-readable storage medium of claim 12, wherein determining a value of one or more parameters of the diffracting structure using the stored model includes:

performing a computation of at least one physical characteristic of the diffracting structure based on the measured optical reflectance data using the stored model.

* * * * *